(12) United States Patent
Jacoby et al.

(10) Patent No.: US 11,266,769 B2
(45) Date of Patent: Mar. 8, 2022

(54) SLEEVE FOR MEDICAL DEVICE ASSEMBLY

(71) Applicant: W. L. Gore & Associates, Inc., Newark, DE (US)

(72) Inventors: Russell L. Jacoby, Flagstaff, AZ (US); Andrew W. Sloan, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/887,711

(22) Filed: May 29, 2020

(65) Prior Publication Data
US 2020/0289718 A1 Sep. 17, 2020

Related U.S. Application Data

(60) Continuation of application No. 16/025,071, filed on Jul. 2, 2018, now Pat. No. 10,675,388, which is a
(Continued)

(51) Int. Cl.
*A61L 31/14* (2006.01)
*B65B 11/00* (2006.01)
(Continued)

(52) U.S. Cl.
CPC .............. *A61L 31/14* (2013.01); *B29C 53/56* (2013.01); *B29D 23/00* (2013.01); *B65B 11/00* (2013.01);
(Continued)

(58) Field of Classification Search
CPC ... B29C 53/56; B29C 53/20; B29C 2053/365; B29D 23/00; A61L 31/14; A61F 2/97; B65B 11/00; Y10T 428/1393; Y10T 428/24777

USPC ............. 428/36.91, 192, 220, 421; 606/194; 623/1.15, 1.54, 1.44, 1.13; 493/269; 53/461

See application file for complete search history.

(56) References Cited

U.S. PATENT DOCUMENTS

| 4,816,339 A | 3/1989 | Tu et al. |
| 5,484,498 A | 1/1996 | Hogarth et al. |

(Continued)

FOREIGN PATENT DOCUMENTS

WO 98/27893 A2 7/1998

OTHER PUBLICATIONS

International Preliminary Reporton Patentability received for PCT Patent Application No. PCT/US2013/067521, dated May 14, 2015, 5 pages.
(Continued)

*Primary Examiner* — Ruiyun Zhang

(57) ABSTRACT

The present disclosure describes a medical device assembly comprising an expandable medical device wrapped with an improved constraining sleeve. The sleeve in accordance with various embodiments of the present disclosure is thin walled and translucent, having reduced edge sharpness. The sleeve in accordance with the present disclosure exhibits resistance to ripping and delamination. Various embodiments of the present disclosure provide methods of making sheet material usable for constraining sleeves from flattened film tubes. Methods for making improved constraining sleeves and medical device assemblies that comprise an improved constraining sleeve are also disclosed herein.

14 Claims, 7 Drawing Sheets

Related U.S. Application Data division of application No. 14/066,454, filed on Oct. 29, 2013, now Pat. No. 10,010,654.

(60) Provisional application No. 61/720,330, filed on Oct. 30, 2012.

(51) Int. Cl.
  *B29C 53/56* (2006.01)
  *B29D 23/00* (2006.01)
  *B29C 53/20* (2006.01)
  *B29C 53/36* (2006.01)
  *A61F 2/97* (2013.01)

(52) U.S. Cl.
  CPC ................ *A61F 2/97* (2013.01); *B29C 53/20* (2013.01); *B29C 2053/365* (2013.01); *Y10T 428/1393* (2015.01); *Y10T 428/24777* (2015.01)

(56) References Cited

U.S. PATENT DOCUMENTS

| | | |
|---|---|---|
| 5,747,128 A | 5/1998 | Campbell et al. |
| 5,814,405 A | 9/1998 | Branca et al. |
| 6,024,131 A | 2/2000 | Lester et al. |
| 6,027,779 A | 2/2000 | Campbell et al. |
| 6,352,561 B1 | 3/2002 | Leopold et al. |
| 6,827,731 B2 | 12/2004 | Armstrong et al. |
| 6,899,727 B2 | 5/2005 | Armstrong et al. |
| 7,270,870 B2 | 9/2007 | Hetzler et al. |
| 7,291,240 B2 | 11/2007 | Smith et al. |
| 7,472,724 B2 | 1/2009 | Lester et al. |
| 7,947,059 B2 | 5/2011 | Chin et al. |
| 8,066,756 B2 | 11/2011 | Rasmussen et al. |
| 8,114,049 B2 | 2/2012 | Freyman et al. |
| 8,267,988 B2 | 9/2012 | Hamer et al. |
| 8,308,789 B2 | 11/2012 | Armstrong |
| 8,545,544 B2 | 10/2013 | Spenser et al. |
| 8,968,381 B2 | 3/2015 | Parker et al. |
| 9,387,097 B2 | 7/2016 | Eblacas et al. |
| 10,010,654 B2 | 7/2018 | Jacoby et al. |
| 2004/0081784 A1 | 4/2004 | Smith et al. |
| 2006/0015171 A1 | 1/2006 | Armstrong |
| 2008/0237116 A1 | 10/2008 | Bacino et al. |
| 2009/0011851 A1 | 1/2009 | Tanio |
| 2009/0227949 A1 | 9/2009 | Knapp et al. |
| 2009/0254169 A1 | 10/2009 | Spenser et al. |
| 2011/0238041 A1 | 9/2011 | Lim et al. |
| 2012/0059448 A1 | 3/2012 | Parker et al. |
| 2012/0130475 A1 | 5/2012 | Shaw |
| 2014/0066897 A1 | 3/2014 | Campbell et al. |
| 2014/0066898 A1 | 3/2014 | Cully et al. |
| 2018/0311416 A1 | 11/2018 | Jacoby et al. |

OTHER PUBLICATIONS

International Search Report for PCT/US2013/067521 dated Feb. 24, 2014, corresponding to U.S. Appl. No. 14/066,454, 4 pages.

SLEEVE FOR MEDICAL DEVICE ASSEMBLY

CROSS-REFERENCE TO RELATED APPLICATION

This application is a continuation of U.S. application Ser. No. 16/025,071, filed Jul. 2, 2018, now U.S. Pat. No. 10,675,388, granted Jun. 9, 2020, which a divisional of U.S. application Ser. No. 14/066,454, filed Oct. 29, 2013, now U.S. Pat. No. 10,010,654, granted Jul. 3, 2018, which claims the benefit of Provisional Application No. 61/720,330, filed Oct. 30, 2012, which are incorporated herein by reference in their entireties for all purposes.

FIELD

The present disclosure relates in general to medical device assemblies and more particularly to improved constraining members for use in the same.

BACKGROUND

Medical devices are frequently used to treat the anatomy of patients. Examples of such devices include stents, grafts, stent-grafts, filters, valves, occluders, markers, mapping devices, therapeutic agent delivery devices, prostheses, pumps, bandages, and the like. Such devices can be implanted. Such devices can also be expandable and delivered endoluminally. In the latter case, an expandable device, is constrained by a constraining member, such as a sheath or a sleeve, toward a reduced delivery profile suitable for endoluminal delivery on a catheter, introduced into the body at an insertion point, delivered endoluminally toward a treatment site, and expanded at the treatment site.

Although many improvements have been made to medical device assemblies in general, constraining members, configured with sufficient strength to constrain expandable devices, can reduce the flexibility and increase the profile of devices due to the thickness of the materials used. Conversely, thinner walled constraining members can rip apart at stitch lines. Constraining members can burst when used to constrain self-expanding devices to very small delivery profiles.

Therefore, smaller profile medical device assemblies that can be reliably introduced and moved through body conduits such as the vasculature are desired. In particular, thinner and stronger constraining members for use with expandable medical devices are desired.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Figure 1:
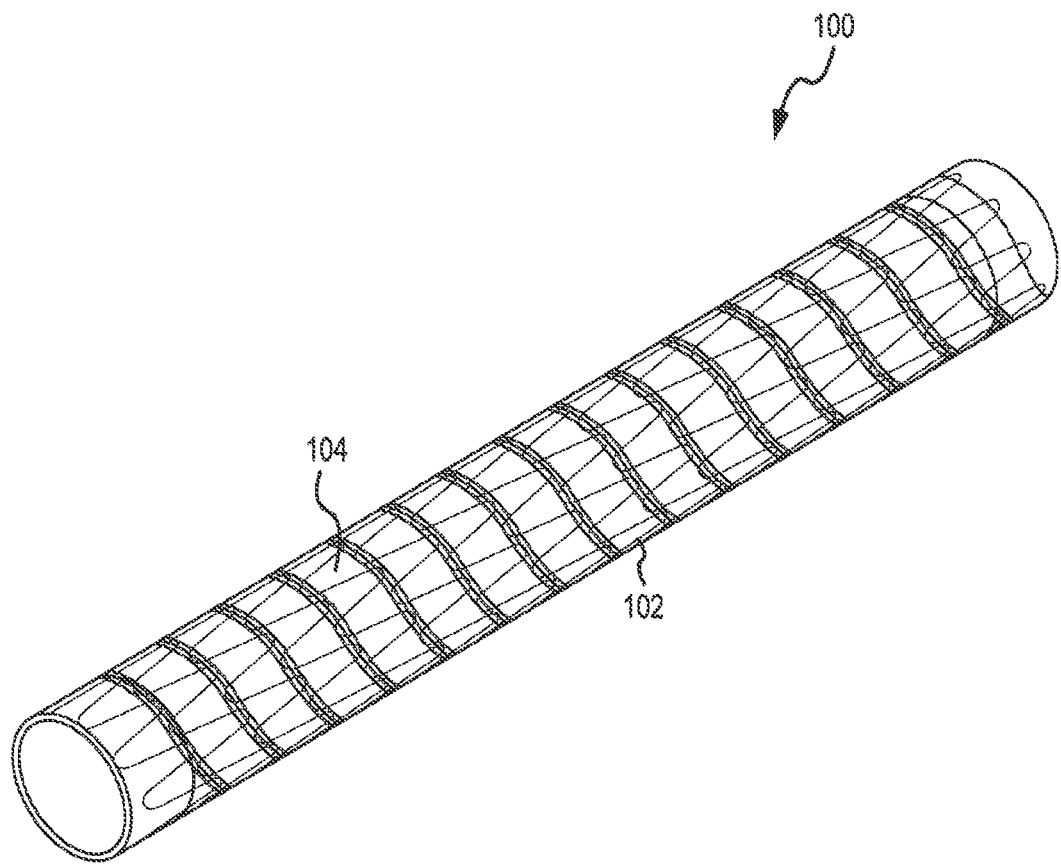
FIG. 1 illustrates a perspective view of an embodiment of an expanded medical device in a collapsed configuration in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

With that said, and as will be described in more detail herein, various embodiments of the present disclosure generally comprise a medical device assembly further comprising an expandable medical device compacted toward a reduced outer peripheral dimension suitable for endoluminal delivery and covered with an improved constraining sleeve. An improved sleeve in accordance with various embodiments of the present disclosure is thin walled and translucent. Furthermore, various embodiment of an improved sleeve exhibit reduced edge sharpness, high strength and resistance to ripping.

Additionally, and as will be described in more detail herein, various embodiments of the present disclosure also comprise methods of manufacturing improved constraining sleeves for use in medical device assemblies, methods of manufacturing sheet material suitable for use in constraining sleeves, and methods of manufacturing medical device assemblies comprising improved constraining sleeves.

As used herein, "medical devices" can include, for example, stents, grafts, stent-grafts, filters, valves, occluders, markers, mapping devices, therapeutic agent delivery devices, prostheses, pumps, bandages, and other endoluminal and implantable devices that are implanted, acutely or chronically, in the vasculature (vessel) or other body lumen or cavity at a treatment region or site. Such medical devices can comprise a flexible material that can provide a fluid-resistant or fluid-proof surface, such as a vessel bypass or blood occlusion.

As used herein, an "expandable implant" can include any medical device deliverable to the treatment site at a compacted delivery profile and capable of dilation from the delivery profile, through a range of intermediary outer peripheral dimensions, and toward a maximal, pre-determined functional outer peripheral dimension. Such expandable devices can include, for example, stents, grafts, and stent-grafts.

As used herein, translucent means semitransparent. Light will pass diffusely or partially through translucent material.

In various embodiments, an expandable implant can comprise a collapsed configuration suitable for endoluminal delivery of the implant toward the treatment area of the vasculature of a patient. Such an expandable implant can be constrained toward a generally radially collapsed configuration and mounted onto a delivery device such as a catheter. The delivery profile or outer peripheral dimension of the expandable implant in the collapsed configuration is preferably small enough for the implant to be delivered through the vasculature to the treatment area. In various embodiments, the outer peripheral dimension of the collapsed configuration is small enough to minimize the crossing profile of a catheter and reduce tissue damage to the patient. In the collapsed configuration, the expandable implant can be guided through the vasculature.

In various embodiments, an expandable implant can comprise a generally radially expanded configuration suitable for implanting the device in the treatment area of a patient's vasculature. In the expanded configuration, the outer peripheral dimension of an expandable implant can approximate the vessel to be repaired. In other embodiments, the outer peripheral dimension of expandable implant in the expanded configuration can be slightly larger than the vessel to be treated to provide a traction fit within the vessel.

In various embodiments, an expandable implant can comprise a self-expandable device, such as a self-expandable stent-graft. Such devices dilate from a generally radially collapsed configuration toward a generally radially expanded configuration when unconstrained. As used herein, the term "constrain" can mean (i) to limit expansion, occurring either through self-expansion or expansion assisted by a device, of an expandable implant, or (ii) to cover or surround, but not otherwise restrain, an expandable implant (e.g., for storage or biocompatibility reasons and/or to provide protection to the expandable implant and/or the vasculature).

In various embodiments, an expandable implant can comprise a device that is expanded with the assistance of a secondary device such as, for example, a balloon.

In various embodiments, an expandable implant can comprise a stent-graft. Stent-grafts are designed to generally comprise one or more stent components that form a support structure or scaffold, with one or more graft members displaced over and/or under the stent.

In various embodiments, the support structure can comprise, for example, a plurality of stent rings, cut tubes, wound wires (or ribbons) or flat patterned sheets rolled into a tubular form. Stent rings can be operatively coupled to one another with a wire. A wire used to couple stent rings can attach to the peak of a first stent ring and a valley of a second stent ring. The stent ring can be arranged such that the peaks in valleys are in-phase (e.g., the peaks of the first stent ring share a common centerline with the peaks of the second stent ring) or out of phase (e.g., the peaks of the first stent ring share a common centerline with the valleys of the second stent ring).

Stent components for support structure can be formed from metallic, polymeric or natural materials, and can comprise conventional medical grade materials such as for example nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as iron alloys, stainless steels, cobalt-chromium alloys, nitinol, and the like; and biologically derived materials such as bovine arteries/veins, pericardium and collagen. Stent components can also comprise bioresorbable organic materials such as poly(amino acids), poly(anhydrides), poly(caprolactones), poly(lactic/glycolic acid) polymers, poly(hydroxybutyrates) and poly(orthoesters). Any expandable stent component configuration that can be delivered to a treatment site is in accordance with the present disclosure.

In various embodiments, graft materials in stent-grafts can include, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aramid fibers, and combinations thereof. Other embodiments for a graft member material can include high strength polymer fibers such as ultra-high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof. Any graft member that can be delivered in a patient to a treatment site is in accordance with the present disclosure.

In various embodiments, a stent component and/or graft member can comprise a therapeutic coating. In these embodiments, the interior or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, an expandable implant such as a stent-graft can be constrained by a constraining member or a "sleeve," which peripherally surrounds the expandable implant. In various embodiments, a sleeve peripherally surrounds an expandable implant and constrains it toward a collapsed configuration in which the outer peripheral dimension is less than the outer peripheral dimension of the unconstrained implant. For example, a sleeve can constrain an expandable implant toward a collapsed configuration or outer peripheral dimension suitable for endoluminal delivery toward a treatment site within the vasculature.

In various embodiments, sleeves can be tubular and serve to constrain an expandable implant such as a stent-graft. In such configurations, sleeves are formed from at least one sheet material wrapped or folded about the expandable implant. While the illustrative embodiments herein are described as comprising one or more tubular sleeves, sleeves of any non-tubular shape that correspond to an underlying expandable implant or that are otherwise appropriately shaped for a given application are also within the scope of the present disclosure.

In various embodiments, sleeves can comprise materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenylene Ether (Mod PPE),Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA).

In various embodiments, tape can comprise any of the above-listed materials or combinations thereof, and in various embodiments, such tape can be used to build layers that are laminated together into sheet material for sleeves. Examples of laminated materials, such as PTFE film laminated to another substrate, can be found in U.S. Pat. No. 7,521,010 to Kennedy et al., the content of which is incorporated herein by reference in its entirety.

In various embodiments, sleeves are formed by wrapping sheet material such that two opposing and/or parallel edges of the sheet are substantially aligned. The alignment may or may not be parallel to or coaxial with the catheter shaft of a catheter assembly. In various embodiments, the edges of the sheet material(s) do not contact each other.

In various embodiments, the edges of the sheet material(s) contact each other and are coupled together with an elongated coupling member, as described below. In various other embodiments, the edges of the sheet material(s) are aligned so that the edges of the same side of the sheet or sheets (e.g., the front or back of the sheet) are in contact with each other. In still other embodiments, the edges of opposite sides of the sheet material(s) are in contact with each other, such that the edges overlap each other, such that a portion of one side of the sheet is in contact with a portion of the other side. Said another way, the front of the sheet can overlap the rear of the sheet, or vice versa.

In various embodiments, the sheet material includes a row of openings perforated by any method along each opposing edge, which are configured to accommodate the elongated coupling member such that the elongated coupling member can secure the sheet material into a tubular shape around the expandable device. In various embodiments of an improved sleeve, reinforcement fibers, or other similar materials or compounds, can be provided to prevent the elongated coupling member from ripping through the sleeve proximate to the openings.

For example, in various embodiments, sleeves used to constrain expandable implants further comprise any number of reinforcing fibers. In such embodiments, fibers are laid onto, or embedded into, sheet material used to form the sleeve. Reinforcing fibers can be comprised of any suitable flexible strand possessing high-strength and minimal elongation as known in the art. In various embodiments, a high-strength fiber can have a tensile strength ranging from about 0.5 Gpa to about 2.5 Gpa or higher, and can have an elongation to break of less than about 5%. Exemplary reinforcing fibers include, but are not limited to, polyethylene fiber, polyimide fiber, ePTFE fiber such as KORETEK®, polyether fiber such as polyethylene terephthalate (DACRON® or MYLAR®), polyacrylamide fiber such as KEVLAR®, liquid crystal polymer fiber, and metal fiber such as nitinol, stainless steel, or gold, and combinations thereof.

In various embodiments, the reinforcing fiber or fibers within a constraining sleeve can have varied diameters and/or cross-sectional profiles. For example, the fibers can have a circular cross-section with a diameter ranging from about 0.0001 mm to about 1 mm. In various embodiments, the fibers can have a circular cross section of about 0.01 mm to about 0.1 mm. In various embodiments, the fibers can have a circular cross-section of about 0.03 mm to about 0.05 mm. In addition, reinforcing fibers can have a non-circular cross-section, such as, for example, a triangle, rectangle, square or other geometric shape. Moreover, the geometry of the one or more reinforcing fibers present in a constraining sleeve can be the same or varied. For example, circumferentially oriented fibers can have a substantially flat cross-section, whereas longitudinally oriented fibers can have a substantially circular cross-section.

In various embodiments, sleeves used to constrain expandable implants can further comprise radiopaque or echogenic markers. In such configurations, radiopaque markers can be located at the edges of sleeves, in the region where a coupling member is stitched through the series of openings. Radiopaque markers can assist in the positioning and orientation of the expandable implant within a vasculature, for example, by increasing the visibility through imaging of the location and orientation of elements such as sleeves, coupling members, side branches, fenestrations, fenestratable areas, cuffs, anchors, and the like.

As used herein, "deployment" refers to the actuation of the medical device at or near a treatment site, such as for example, the removal of a sleeve on a self-expandable implant to allow the implant to expand. Upon such deployment, the sleeve or sleeves can be removed to allow the expandable implant to expand toward a functional or deployed outer peripheral dimension and achieve a desired therapeutic outcome. In some embodiments, the sleeve or sleeves can remain implanted while not interfering with the expandable implant. In other embodiments, the sleeve or sleeves can be removed.

In various embodiments, deployment of a self-expandable stent-graft can comprise pulling out a coupling member that was used in securing the sleeve over the stent-graft, maintaining it in a collapsed configuration. This process of removing the coupling member from the sleeve is also referred to herein as "disengagement." Examples of constraining members and coupling members for releasably maintaining expandable devices in a collapsed state for endoluminal delivery can be found in U.S. Pat. No. 6,352,561 to Leopold et al., the content of which is incorporated herein by reference in its entirety.

In various embodiments, when the expandable implant, such as a stent-graft, is in position within the vasculature, the coupling member can be disengaged from the sleeve from outside of the body of the patient, which allows the sleeve to open and the expandable implant to expand. As discussed above, the expandable implant can be self-expanding, or the implant can be expanded by a second device, such as a balloon. The coupling member can be disengaged from the sleeve by a mechanical arrangement operated from outside of the body of the patient. For example, the coupling member can be disengaged by applying sufficient tension to the member. In another example, a dial, rotational element, or any suitable actuation member can be operatively connected to the coupling member outside of the body such that rotation or actuation of the dial or rotational element or actuation member provides sufficient tension to disengage the coupling member.

In various embodiments, a sleeve and a method of making the same is disclosed herein, which can result in constraining sleeves that are thin and translucent, have reduced edge sharpness, and yet maintain high burst strength and resistance to ripping or stitch line pull out.

The above being noted, with reference now to FIG. 1, a medical device 100 in accordance with the present disclosure is illustrated. Medical device 100 comprises a stent 102 and a graft member 104. In various embodiments, graft member 104 is affixed to the outside surface of stent 102 such that once deployed, graft member 104 is placed into contact with a vessel wall. In other embodiments, graft member 104 is affixed to the inside surface of stent 102.

Figure 2:
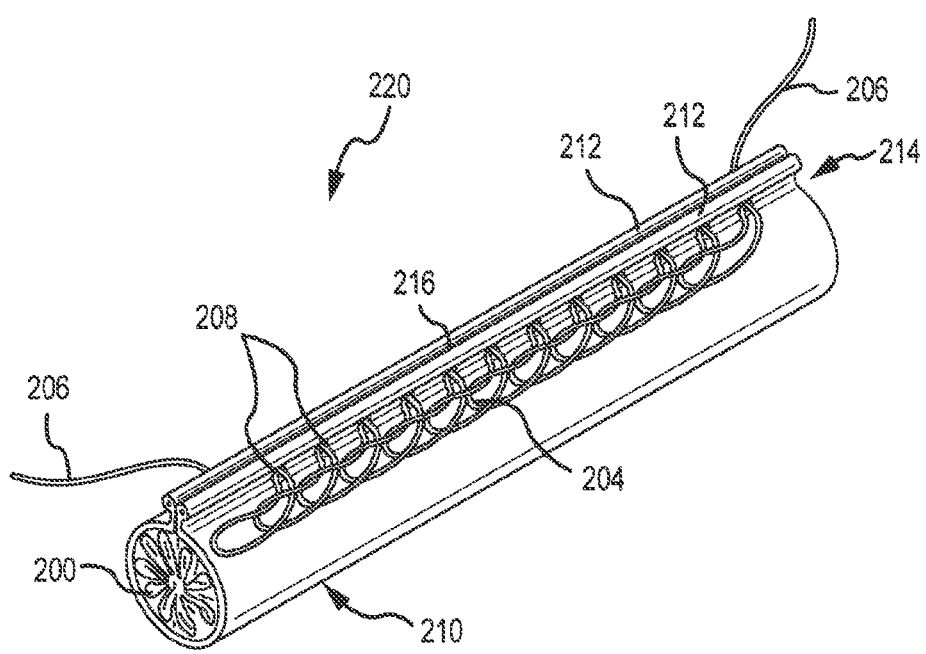
FIG. 2 illustrates a perspective view of an embodiment of an expandable medical device constrained in a collapsed configuration in accordance with the present disclosure.

Referring now to FIG. 2, an embodiment of a medical device assembly 220 in accordance with the present disclosure comprises an expandable device 200, such as a stent graft. The expandable device 200 is compacted or constrained by a constraining member or sleeve 210 toward a reduced outer peripheral dimension suitable for endoluminal delivery of the device to a treatment site. In various embodiments, constraining members such as constraining sleeve 210 can comprise materials similar to those used to form a graft member. As will be discussed below, flattened thin wall ePTFE film tubes provide suitable starting material for sleeve 210. The constraining sleeve 210, when made in accordance with the present disclosure, can be thin walled. Such a thin walled constraining sleeve 210 may add only minimally to the total delivery profile of the device, yet still be strong enough to securely constrain an expandable device toward a reduced outer peripheral dimension.

In the embodiment illustrated in FIG. 2, the sleeve 210 includes generally opposite and/or parallel edges or portions 212 each with a plurality of openings 208 such as eyelets. The openings 208 are arranged in rows to form stitch lines 214 extending along the opposite portions 212 of the sleeve 210. The sleeve 210 extends around the device 200, with the opposing portions releasably secured together to define a releasable seam 216 that runs axially along the length of the sleeve 210. In this case, a flat sheet material can be wrapped circumferentially around the device for closure to form such a seam.

In various embodiments, the releasable seam 216 can be held together by an elongated coupling member 206 extending through or woven through the openings 208. The threading or weave can comprise any variation of stitching, such as for example a chain stitch comprising individual slip knots or loops 204 that are interconnected. In various embodiments, the coupling member 206 can comprise a woven fiber. In other embodiments, the coupling member 206 can comprise a monofilament fiber. Any type of string, cord, thread, fiber, or wire capable of maintaining a sleeve in a tubular shape is within the scope of the present disclosure. The coupling member 206 can comprise ePTFE fiber such as KORETEK®, sutures of polyethers such as polyethylene terephthalate (DACRON® or MYLAR®) or polyacrylamides such as KEVLAR®. The coupling member 206 can alternatively comprise a metal wire made from nitinol, stainless steel, or gold. In various embodiments, the coupling member 206 can extend long enough to form a remote pull line or can be coupled to a separate pull line of the same or different material.

In various embodiments, when the expandable device 200 is in position at or near the treatment site of the patient, the elongated coupling member or members 206 can be disengaged from the sleeve or sleeves 210 from outside of the body of the patient, which allows the sleeve(s) to open and the expandable device 200 to expand.

In various embodiments, the coupling member 206 can extend through a catheter shaft and be accessed by a clinician through proximal connectors. Tensioning, actuation and displacement of the coupling member 206 from the openings 208 allows the sleeve 210 to open along the releasable seam 216 and for the device 200 to expand from a reduced outer peripheral dimension suitable for endoluminal delivery to a treatment site toward a larger outer peripheral dimension during deployment at or near the treatment site.

Figure 3:
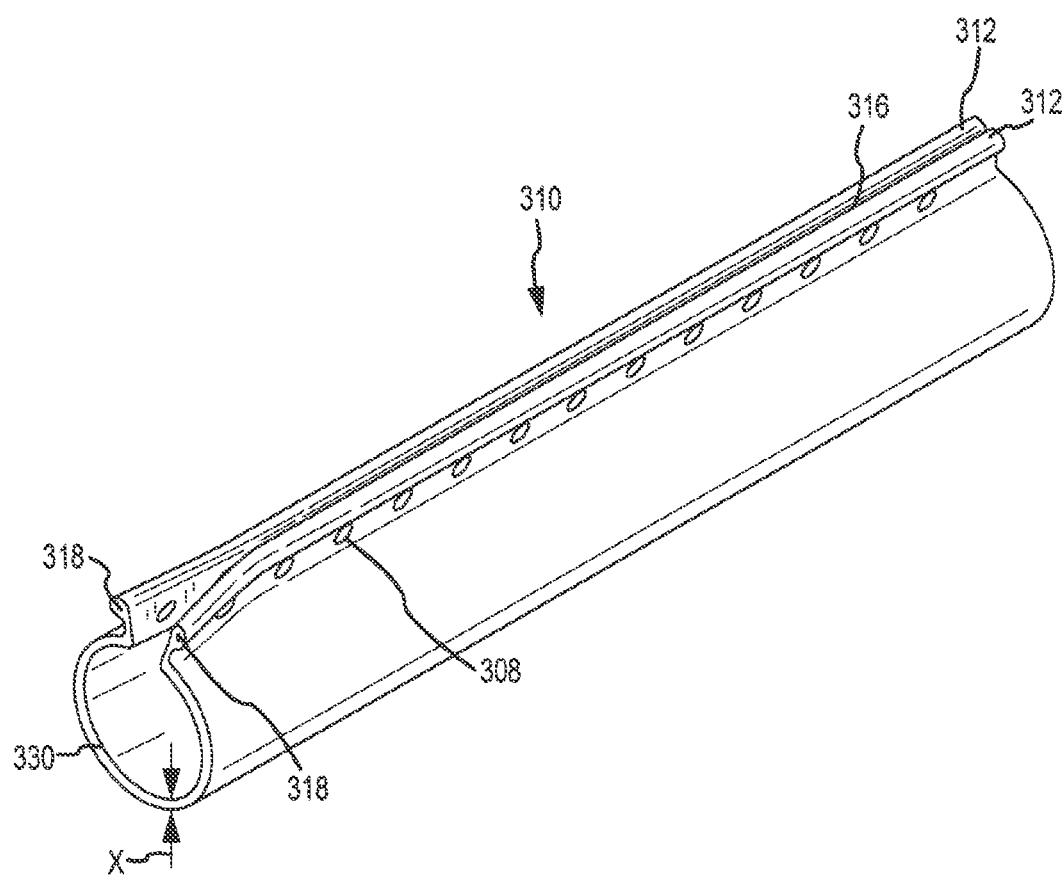
FIG. 3 illustrates a perspective view of an embodiment of a tubular coaxial constraining sleeve in accordance with the present disclosure.

Referring now to FIG. 3, a perspective view of an embodiment of a constraining sleeve 310 in accordance with the present disclosure is illustrated. Sleeve 310 can be substantially tubular to fit generally coaxially over an expandable device in a medical device assembly. The tubular shape can be obtained by wrapping sheet material 330 around the device and bringing opposing ends 312 into close proximity for coupling. The wrapping of sheet material 330 to form the tubular sleeve 310 can be concomitant with the compression of an expandable device to a compact or reduced outer peripheral dimension, or it can be at any other time during the process of assembling a medical device assembly. The tubular sleeve 310 can include rows of openings 308. The openings 308 can be configured through the sleeve 310 at any time during the manufacturing of the sheet material 330 or at any other time during the process of assembling the medical device assembly.

Still referring to FIG. 3, a sleeve 310 in accordance with the present disclosure includes at least one reinforcing fiber 318 substantially embedded within sheet material 330 as illustrated. Such embedding of the fiber(s) 318 can be accomplished by thermal, ultrasonic, ultraviolet, or solvent bonding of layers of sheet material with the fiber(s) placed on, or sandwiched between, layers of sheet material. Such bonding results in a flow of sheet material over and around the one or more reinforcing fibers, thereby encasing the fiber(s). The one or more reinforcing fibers 318 extend along at least one of the opposing ends 312 of the shaped sleeve 310, as in the embodiment illustrated. As discussed above, in various embodiments, the tubular constraining sleeve 310 includes two rows of openings 308 positioned along opposing ends 312 of the sheet material that can be used for securing the sleeve 310 with an elongated coupling member. A reinforcing fiber 318 is disposed within the sheet material 330 along each of the two opposing ends 312 such that the two fibers 318 strengthen the releasable seam 316 once the opposing ends 312 are coupled together by an elongated coupling member woven through the openings 308. Disposed longitudinally between the row of openings 308 and the edge 312, each reinforcing fiber 318 acts as a rip-stop, preventing the elongated coupling member from tearing through the sheet material 330 proximate to the openings 308.

With continued reference to FIG. 3, a sleeve 310 constructed in accordance with the present disclosure can have minimal edge sharpness along both opposing edges 312.

Additionally, sleeve 310 can have a final wall thickness x of less than about 0.12 mm. In various embodiments, thickness x is less than about 0.10 mm. In various embodiments, thickness x ranges between about 0.08 and about 0.10 mm. The final wall thickness x of the sheet material 330 used for the sleeve 310 can arise from any number of precursor layers of sheet material, such as ePTFE, which can be bonded to create the finished sheet material 330. With bonding of precursor layers, any separate layers that may have contributed to the finished sheet material 330 may or may not be discernible on either end of the sleeve 310 or in any cross-sectional cut made through the sleeve 310.

In various embodiments, sleeve 310 in FIG. 3 is translucent, allowing a light transmission of 80% or greater, or 90% or greater, or 95% or greater over a wide spectrum of incident wavelengths. A translucent sleeve allows a view of the expandable device through the sleeve, which is particularly advantageous during assembly of the sleeve and the constrained device.

In various embodiments and with reference to FIG. 3, sleeve 310 exhibits high burst strength and a high resistance to ripping of sheet material 330 proximate to the openings 308. Burst strength and tensile strength measurements are detailed below.

Figure 4:
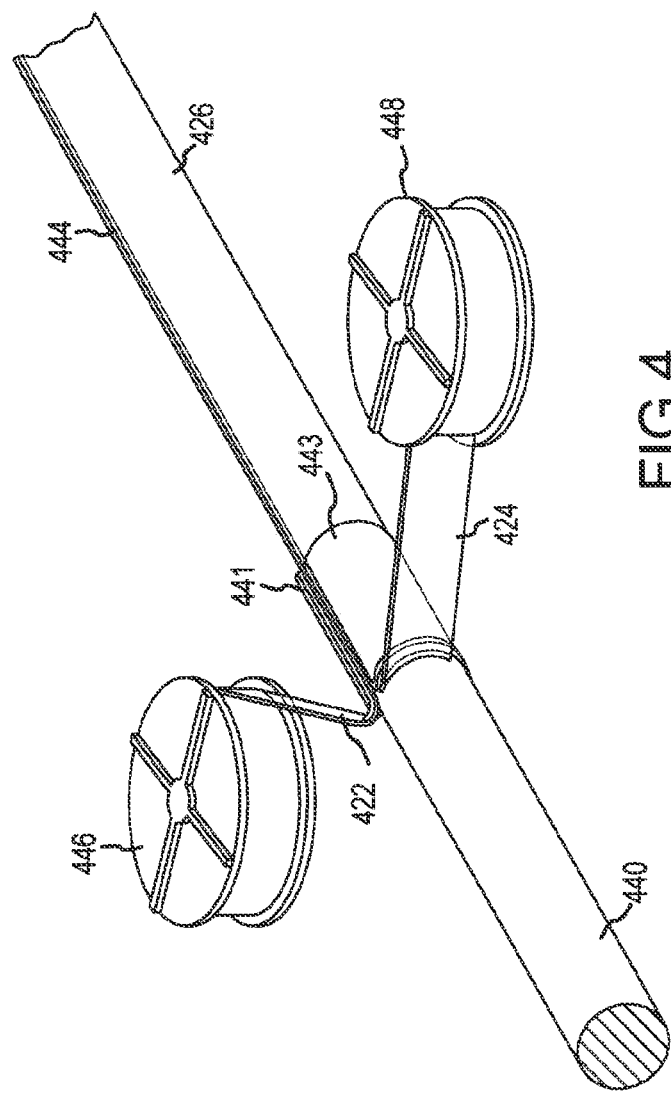
FIG. 4 illustrates a perspective view of an embodiment of a longitudinal tape wrapping process in accordance with the present disclosure.

Referring now to FIG. 4, an embodiment of a method of manufacturing a constraining sleeve in accordance with the present disclosure is illustrated. Spools 446 and 448 are used to supply tape 422 and 424 to generally opposite sides of a longitudinally presented rod or mandrel 440. In various embodiments, tape for this process can comprise any combination of materials used for tape as discussed above, such as ePTFE optionally coated at least partially on one or both sides with an adhesive material such as fluorinated ethylene propylene (FEP). Methods of making ePTFE sheets or tape can be found in U.S. Pat. No. 5,792,525 to Fuhr et al., the content of which is incorporated herein by reference in its entirety. The mandrel 440 can be heated intermittently or continuously to bond together the longitudinal wrappings of tape into a tubular film layer 426. The mandrel 440 can be heated utilizing any suitable means, such as by conductive or inductive heating. An induction heater, for example as produced by Ambrell®, can be used to heat the mandrel to at least about 300° C. when the tape has begun to wrap correctly.

As illustrated in FIG. 4, generally longitudinal placement or application of tape 422 and 424 can be assisted by guides 441 and 443 that slide along the mandrel 440 in an automated process. Guides 441 and 443 can be used to push the tape 422 and 424 firmly toward the mandrel 440 and assist in bonding overlapped portions of tape into longitudinal seams 444. The guides can also be heated for this purpose. The finished tubular layer of film 426 thus formed can comprise any number of overlapping tape portions. When two longitudinally overlapping tapes are used, the sum of the widths of tape 422 and tape 424 are greater than the circumference of the mandrel 440 such that the two opposing runs of tape will overlap on the mandrel to form longitudinal seams 444. Any number of first layers of film can be produced in this manner, using tape fed in from any direction and from any number of spools. Although the wrapping of tape is illustrated in FIG. 4 as longitudinal in orientation, the first layer(s) of film 426 can be made by any combination of longitudinal or cigarette wrapping, radial or helical winding. In various embodiments, the orientation of the wrapping of the tape and hence, the longitudinal or machine direction, can be chosen to give one or more different characteristics to the film layer produced from the wrappings. For example, the burst strength of a film layer can be improved by increasing the angle of wrapping relative to the longitudinal axis of the mandrel. The process of wrapping tape on a mandrel to produce film tubes can be an entirely manual, partially automated, or fully automated process, as deemed appropriate.

Figure 5:
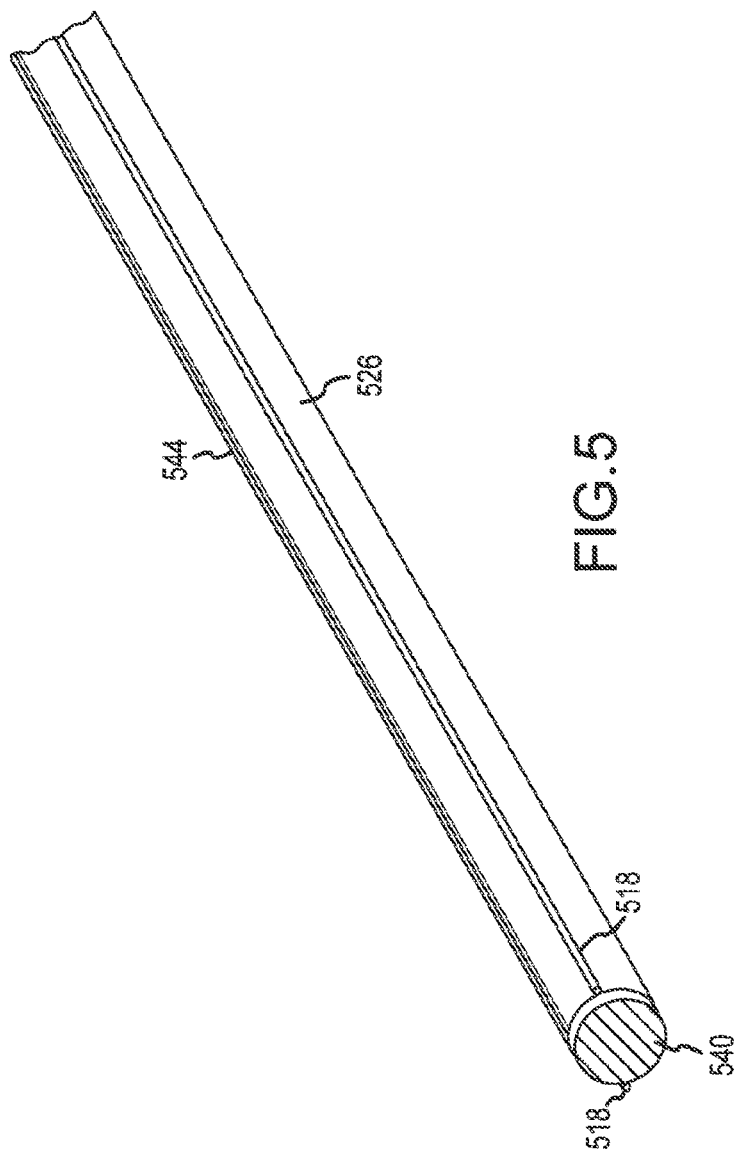
FIG. 5 illustrates a perspective view of an embodiment of a partially formed film tube in accordance with the present disclosure.

Referring now to FIG. 5, at least one reinforcing fiber 518 is positioned against the at least one layer of film 526 that was produced by wrapping tape on the mandrel 540. The one or more fibers 518 can be positioned on the mandrel 540 in any direction as needed. In the embodiment illustrated, two lengths of reinforcing fiber 518 are positioned longitudinally down the cylindrical mandrel 540 generally parallel to both the overlapped tape seam 544 and to each other. When two fibers 518 are utilized in this manner, they are disposed on opposite sides of the mandrel as close as possible to a 180° separation from one another along the length of the mandrel. As discussed below, once the one or more reinforcing fibers 518 are positioned against the first layer(s) of film 526, additional windings of tape can then be wound in order to sandwich these fibers between film layers and build a film tube.

Figure 6:
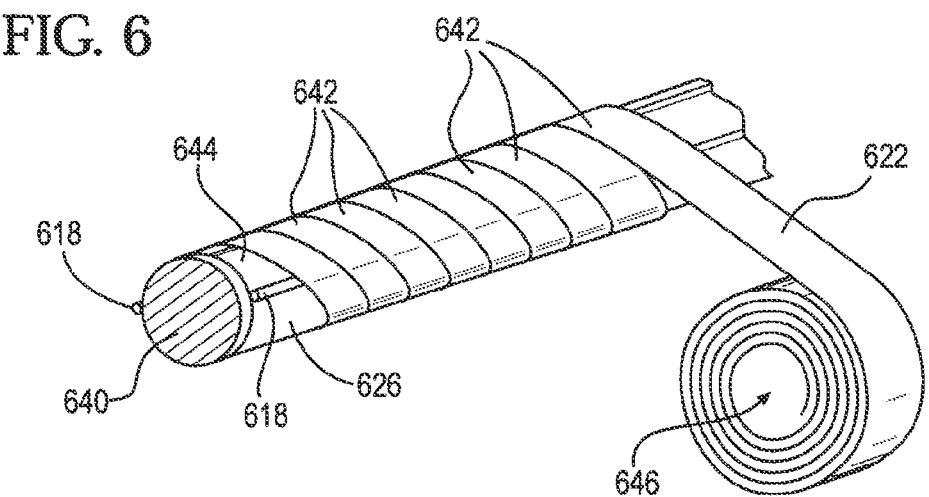
FIG. 6 illustrates a perspective view of an embodiment of a helical tape wrapping process in accordance with the present disclosure.

Referring now to FIG. 6, tape 622 is applied around the mandrel 640 to form any number of additional layers to the film tube. In various embodiments, tape 622 can be formed from ePTFE, which can be coated at least partially on at least one side with an adhesive material such as fluorinated ethylene propylene (FEP) for bonding of tape 622 to the first film layer(s) 626 and fibers 618. Although helical winding is illustrated, windings 642 can comprise any combination of longitudinal, helical or radial winding, with any degree of overlap in the windings. For example, it can be desirable to wrap a number of helical windings at a particular pitch angle and overlap, and then add radial windings to bolster the radial strength of the finished film tube. As illustrated, additional windings 642 of tape 622 sandwich the one or more fibers 618 between first film layer(s) 626 and the additional windings 642. For creating additional layers of film, tape 622 can be fed to the mandrel 640 from one or more spools 646 appropriately positioned for the desired tape orientation. The mandrel 640 can be heated, intermittently or continuously, at any time during or after the application tape 622 over the fibers 618. Heating will bond the windings 642 into new layers of film that will bond together with the first film layer(s) 626 to form a single laminate that resists delamination. In the resulting laminate, the reinforcing fibers 618 will be embedded within the film composite. The completed, bonded and reinforced film tube can then be removed from the mandrel.

Figure 7A:
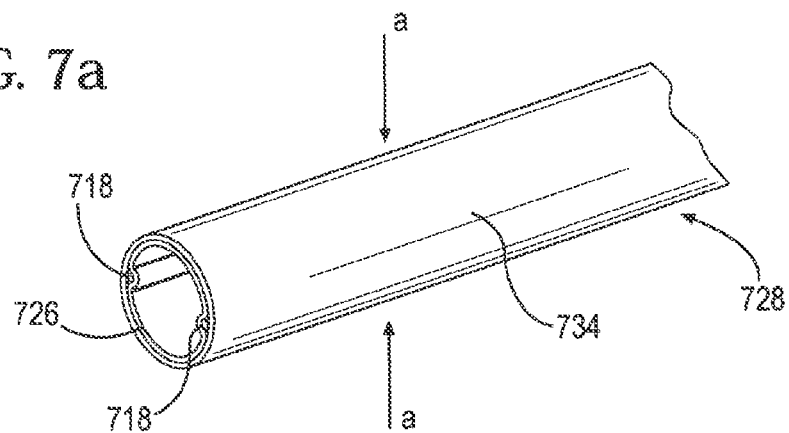
FIG. 7a illustrates a perspective view of an embodiment of a film tube in accordance with the present disclosure.

Referring now to FIG. 7a, an embodiment of a completed film tube 728 in accordance with the present disclosure is illustrated. In this embodiment, film tube 728 comprises two longitudinally oriented reinforcing fibers 718 positioned approximately opposite one another down the length of the tubular structure, sandwiched between bonded film layer(s) 726 and layer(s) 734 and embedded therein. Opposing directional arrows "a" show the direction of force used to flatten the film tube 728 into a flattened film tube usable as a precursor to a tubular constraining sleeve, (FIG. 7b).

Figure 7B:
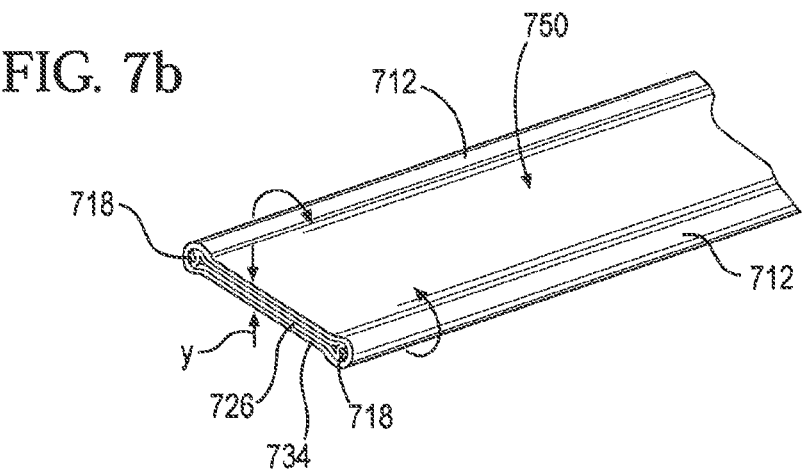
FIG. 7b illustrates a perspective view of an embodiment of a flattened film tube in accordance with the present disclosure.

Referring now to FIG. 7b, an embodiment of a flattened film tube 730 in accordance with the present disclosure is illustrated. The film tube prior to flattening (728 in FIG. 7a) can be flattened when it emerges in a heated condition from the mandrel such that the film tube walls bond together when the tube is flattened. Alternatively, the tube can be flattened and bonded in a subsequent and separate operation using any necessary degree of heat and pressure to flatten the film tube and internally bond the opposing walls of the tube together. When the film tube (728 in FIG. 7a) is properly flattened, the embedded parallel fibers 718 will end up disposed along opposite edges of sheet material 750 without any appreciable salvage hanging beyond substantially parallel boundaries marked by the reinforcing fibers 718. In various embodiments, a resulting flattened tube 730 and final sheet material 750 can be generally translucent and have a thickness y of less than about 0.12 mm. In still other embodiments, thickness y is less than about 0.10 mm. In yet other embodiments, thickness y is from about 0.08 to about 0.10 mm.

Figure 7C:
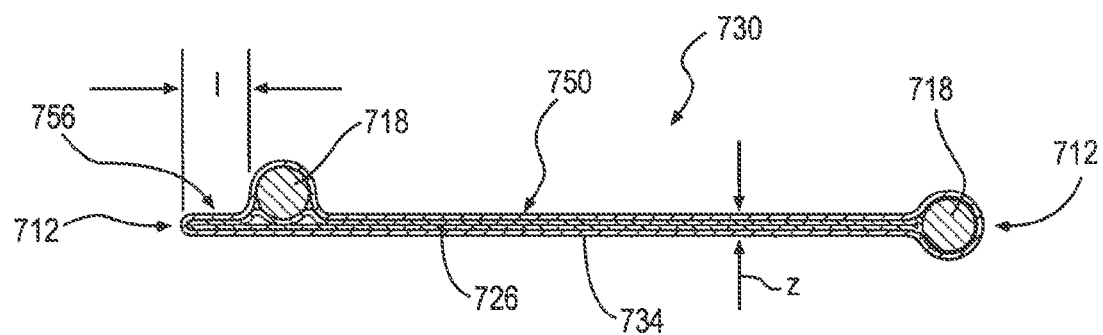
FIG. 7c illustrates a cross sectional view of an embodiment of a flattened film tube in accordance with the present disclosure.

Referring now to FIG. 7c, a cross-section of an embodiment of a flattened tube 730 in accordance with the present disclosure is illustrated. The parallel reinforcing fibers 718 are left sandwiched and bonded between the outer 734 and inner 726 film layers of the sheet material 750 as illustrated. The sandwiching of the fibers 718 resulted from winding at least one first layer of tape on the mandrel; laying down the reinforcing fibers along the mandrel over the at least one first layer of tape; winding additional layers of tape wound onto the mandrel over the reinforcing fibers and the at least one first layer of tape thereby sandwiching the fibers 718 between film layers on the mandrel; and bonding embedded the fibers therein. The ability to discern layers at the ends of the flattened tube or in a cross-section cut through the flattened tube (such as FIG. 7c) generally depends on the degree of bonding of the layers. Thickness z can also depend on any later processing of the flattened film tube 730, such as further heat or solvent bonding.

Still referring to FIG. 7c, excess film material 756 can extend to a length Ion either or both of the opposing ends 712 of the sheet material 750 beyond the boundaries of the reinforcing fibers 718. In various embodiments, length I on either opposing edge 712 is no longer than about 0.5 mm. The flattened film tube 730 thus formed will have little to no sharpness discernible along either opposing edge 712, and each edge 712 will appear rounded with the fiber 718 being the axial core of each rounded edge.

Figure 7D:
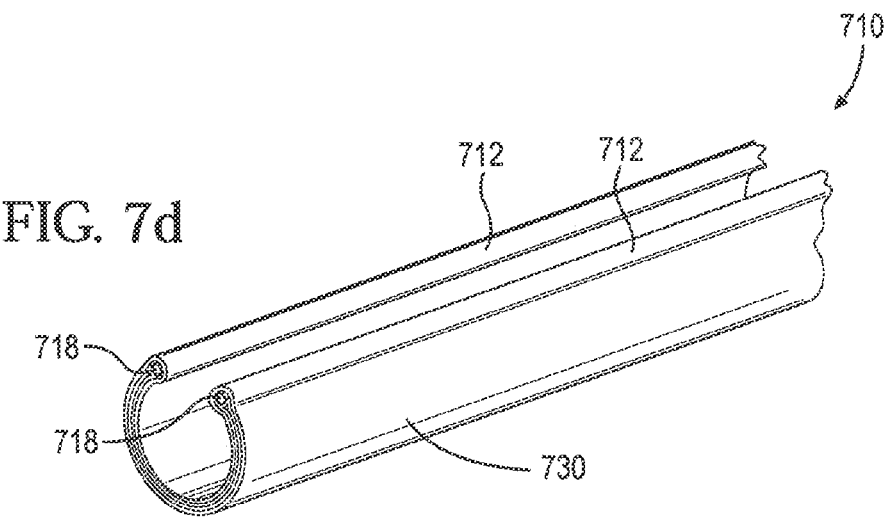
FIG. 7d illustrates a perspective view of an embodiment of a tubular coaxial sleeve in accordance with the present disclosure.

Referring now to FIG. 7d, an embodiment of a tubular sleeve 710 in accordance with the present disclosure can be formed from the flattened and bonded tube 730 by bringing the end portions 712 of the flattened tube 730 into close proximity while shaping the flattened tube 730 into a tubular configuration. The shaping can be facilitated by use of a cylindrical substrate such as a rod or mandrel, or alternatively the flattened tube 730 can be circumferentially wrapped around an expandable device that is compacted toward a reduced or compacted outer peripheral dimension suitable for endoluminal delivery.

An embodiment of an improved constraining sleeve and methods of testing the same in accordance with the present disclosure is described in conjunction with the following examples.

EXAMPLE 1

A constraining sleeve, in accordance with various embodiments, was fabricated by the following process:

1) A steel mandrel was supplied having a diameter of about 12.4 mm (0.49") and a length of about 30 cm (11.8").

2) Four strips of film were then placed onto the mandrel, oriented longitudinally along the length of the mandrel. The film had a width of about 22.2 mm (0.875"), a length of about 30 cm (11.8"). The individual film strips were oriented about 90° to each other with an edge to edge overlap of about 2.8 mm (0.11"). The film was comprised of non-porous ePTFE provided with an adhesive coating (applied to one side of the film) of thermoplastic fluorinated ethylene propylene (FEP). The FEP was oriented out and opposite of the mandrel surface. ePTFE is well known in the medical device arts; it is generally made as described by U.S. Pat. Nos. 3,953,566 and 4,187,390 to Gore. The particular tape described herein was slit from a substantially non-porous ePTFE/FEP film having a thickness of about 0.0064 mm, an isopropyl bubble point of greater than about 0.6 MPa, a Gurley No. (permeability) of greater than 60 (minute/1 square inch/100 cc); (or 60 (minute/6.45 square cm/100 cc)), a density of 2.15 g/cc and a tensile strength of about 309 MPa in the longitudinal length direction (i.e., the strongest direction). The film ends were then secured to the mandrel by an ePTFE suture.

3) A rip stop fiber was formed using the film described in Step 2). About 60 cm (23.6") of the film was twisted into a fiber. The twisted fiber was then heat treated in an air convection oven at about 320° C. for about 5 minutes to reflow the FEP.

4) Two 30 cm (11.8") long rip stop fibers from Step 3) were then placed longitudinally along the mandrel/film strips from Step 2). The rip stop fibers were orientated about 180° from each other. The rip stop fiber ends were then secured to the mandrel by an ePTFE suture.

5) A first layer of film was then helically wrapped onto the mandrel/longitudinal film layers and the rip stop fibers. The film (as described in Step 2) had a width of about 25.4 mm (1.0") and was wrapped at an angle of about 33°. The film edges overlapped by about 4.2 mm (0.16"). The first helical film layer was applied in a single, left to right pass. The FEP was oriented out and opposite of the mandrel surface. The film ends were then secured to the mandrel by an ePTFE suture.

6) A second layer of film was then helically wrapped onto the first helically wrapped film in a single right to left pass. The second helical film was wrapped at an angle of about 12°. The film edges overlapped by about 0.44 mm (0.017"). The FEP was oriented in towards the mandrel surface. The film ends were then secured to the mandrel by an ePTFE suture.

7) The mandrel/film layers and rip stop fibers were then heat treated in an air convection oven at about 320° C. for about 10 minutes to reflow the FEP and bond the assembly together.

The resulting tube, as illustrated in FIG. 7a, can be flattened and formed into a sleeve, as previously described in connection with FIGS. 7b-7d.

EXAMPLE 2

It should be appreciated that the mechanical properties of sleeves can be evaluated using commonly known methods such as tensile tests, thickness measurements, density measurements, burst measurements, optical evaluations, and the like. A tensile test can quantify the resistance to ripping at edges of a sleeve, which is another measure of sleeve strength. The following test methods can, for example, be used to evaluate the sleeve.

Thickness

The thickness of the sleeve was measured using a Starrett snap gauge.

Translucency

The translucency of a sleeve can be measured using a spectrophotometer that records the percent light transmission (% T) through a sleeve across the visible light spectrum.

Tensile Strength

Tensile strength was measured using an Instron® Model 4501 vertical pull tester, (Instron, Norwood, Mass.), with the clamping jaws of the tester interlocked into a modified set of upper and lower clamps used to grip the sleeve on each of the opposing edges. The modified clamps include two parallel rows of 24 tapered needle pins spaced 2.1 mm apart, each pin having an end diameter of about 0.53 mm and a height of about 0.18 mm. The rows of needle pins pierce and hold each opposing edge of the sleeve. The upper set of clamps aid in piercing the sleeve and to prevent the pins from bending during the test. The sleeve is positioned in the set of clamps with the reinforcing fibers of the sleeve behind the rows of pins, such that the tester pulls against the reinforcing fibers embedded in the opposing edges of the sleeve. In this way, the degree to which the reinforcing fibers act as rip-stops can be evaluated. A 500 kg load cell is used and the sleeve is tensioned at a rate of 20 mm/min until the sleeve rips. The force to failure is reported in kg of force.

Burst Strength

Burst strength was measured by wrapping a sleeve to be tested around an inflatable bladder and securing the seam of the sleeve with an elongated coupling member. The bladder is then inflated until the sleeve bursts. The test can be conducted up to a practical limit of about 400 psi.

A translucent sleeve was made in accordance with the flattened film tube method set out in FIGS. 4 through 7d and discussed above, incorporating two lengths of 0.24 mm diameter reinforcing fiber in the process. Once flattened, the flattened film tube measured 0.09 mm in thickness and about 19 mm in width.

The force to failure for the sleeve was about 70 kg when tested as detailed above.

The sleeve also exhibited a burst strength that exceeded 400 psi (the limit of the test method). Based on this resistance to bursting, it is evident that the sleeve in accordance with the present disclosure is strong in spite of being thin walled.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A biocompatible sheet material comprising:
   a laminate of at least four bonded layers of expanded polytetrafluoroethylene film including two generally parallel and opposing edges; and
   at least two reinforcing fiber embedded between any of the bonded layers, wherein a first one of the at least two reinforcing fibers is disposed along a first one of the two opposing edges and a second one of the reinforcing fibers is disposed along a second one of the opposing edges and parallel to the first one of the at least two reinforcing fibers,
   wherein the sheet material is from about 0.08 mm to about 0.10 mm thick, having a burst strength of 400 psi or greater.

2. The biocompatible sheet material of claim 1, wherein the at least one reinforcing fiber is embedded between the bonded layers such that at least one of the four bonded layers includes a portion that extends beyond a boundary defined by the at least one reinforcing fiber.

3. The biocompatible sheet material of claim 1, wherein the biocompatible sheet material has a visible light transmission of about 80% or greater.

4. The biocompatible sheet material of claim 1, wherein the biocompatible sheet material has a visible light transmission of about 90% or greater.

5. The biocompatible sheet material of claim 1, wherein the biocompatible sheet material has a visible light transmission of about 95% or greater.

6. The biocompatible sheet material of claim 1, wherein the biocompatible sheet material includes two generally parallel and opposing edges having a plurality of openings.

7. The biocompatible sheet material of claim 6, wherein the plurality of openings are arranged in rows forming stitch lines extending along each of the two generally parallel and opposing edges.

8. The biocompatible material of claim 7, wherein the two generally parallel and opposing edges are releasably secured to define a releasable seam.

9. The biocompatible sheet material of claim 1, wherein the laminate and the at least one reinforcing fiber are rolled into a tubular form.

10. The biocompatible sheet material of claim 9, wherein a pair of edges of the laminate are aligned.

11. The biocompatible sheet material of claim 10, wherein the pair of opposing edges of the laminate contact each other.

12. The biocompatible sheet material of claim 10, wherein the pair of opposing edges of the lam inate do not contact each other.

13. A biocompatible sheet material comprising:
   a laminate of at least four bonded layers of film; and
   at least one reinforcing fiber embedded between any of the bonded layers, wherein the at least one reinforcing fiber is embedded between the bonded layers such that at least one of the four bonded layers includes a portion that extends beyond a boundary defined by the at least one reinforcing fiber, the at least one reinforcing fiber being longitudinally oriented along a length of the laminate.

14. A biocompatible sheet material comprising:
   a laminate of at least four bonded layers of film including two opposing edges and defining a flat sheet; and
   at least one reinforcing fiber embedded between any of the bonded layers, wherein the at least one reinforcing fiber is disposed along a first one of the two opposing edges.

* * * * *